(12) United States Patent
Adler

(10) Patent No.: US 7,135,675 B1
(45) Date of Patent: Nov. 14, 2006

(54) MULTI-PIXEL AND MULTI-COLUMN ELECTRON EMISSION INSPECTOR

(75) Inventor: David L. Adler, San Jose, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 172 days.

(21) Appl. No.: 10/702,156

(22) Filed: Nov. 5, 2003

Related U.S. Application Data

(60) Provisional application No. 60/453,178, filed on Mar. 10, 2003.

(51) Int. Cl.
  *G01N 23/00* (2006.01)
(52) U.S. Cl. .................. 250/306; 250/307; 250/310
(58) Field of Classification Search ............. 250/306, 250/307, 310, 311
  See application file for complete search history.

(56) References Cited

U.S. PATENT DOCUMENTS

| | | | |
|---|---|---|---|
| 4,694,178 A * | 9/1987 | Harte | 250/396 R |
| 5,578,821 A | 11/1996 | Meisberger et al. | |
| 5,892,224 A * | 4/1999 | Nakasuji | 250/310 |
| 5,973,323 A | 10/1999 | Adler et al. | |
| 6,476,390 B1* | 11/2002 | Murakoshi et al. | 250/310 |
| 6,509,750 B1* | 1/2003 | Talbot et al. | 324/750 |
| 6,586,733 B1* | 7/2003 | Veneklasen et al. | 250/306 |
| 6,771,806 B1* | 8/2004 | Satya et al. | 382/149 |
| 6,797,955 B1* | 9/2004 | Adler et al. | 250/310 |
| 6,844,550 B1* | 1/2005 | Yin et al. | 250/310 |
| 6,855,929 B1* | 2/2005 | Kimba et al. | 250/310 |
| 2002/0088940 A1* | 7/2002 | Watanabe et al. | 250/310 |
| 2002/0161534 A1* | 10/2002 | Adler et al. | 702/35 |

OTHER PUBLICATIONS

Sky Scalable High Performance Computers by SKYComputers, webpage [online]. Sky Computers, Inc. 2002, [retrieved on Nov. 4, 2002]. Retrieved from the internet: http://www.skycomputers.com/hardware/hpc.html.
Tromp, R.M, "Low-energy electron microscopy", IBM J.RES. Develop, Jul. 2000, pp. 503-516, vol. 44, No. 4, International Business Machines Corporation.
Chang, T.H. Philip, et al. "Multiple Electron-Beam Lithography", pp. 1-26.
Diebold, Alain, et al. "Current State of Defect Review by Electron Beam Tools: A White Paper", Jan. 14, 2000, pp. 1-12, Technology Transfer#00013877 A-Eng., SEMATECH.
Tobin, Kenneth W. "Inspection in Semiconductor Manufacturing", pp. 1-13 (K.W. Tobin submission for: V. Sankaran, C.M. Weber, K.W. Tobin "Inspection in Semiconductor Manufacturing", *Webster's Encyclopedia of Electrical and Electronic Engineering*, vol. 10, pp. 242-262, Wiley & Sons, NY, NY, 1999.
RACEway Interlink Functional Specification, Nov. 8, 2000, pp. 1-104, Mercury Computer Systems, Inc., Chemsford, MA.

* cited by examiner

*Primary Examiner*—Nikita Wells
*Assistant Examiner*—Anthony Quash
(74) *Attorney, Agent, or Firm*—Okamoto & Benedicto LLP

(57) ABSTRACT

One embodiment disclosed pertains to an inspection system for inspecting a specimen. The system includes a plurality of columns for directing a plurality of multi-pixel incident beams onto a plurality of multiple-pixel regions of the specimen. Impingement of said incident beams causes emission of electrons from the regions. The system further includes a plurality of multiple-pixel electron detectors, each said detector configured to detect in parallel electrons emitted from a plurality of pixels in one of the regions, and a plurality of processing sub-systems. Each said sub-system is configured to process data from one of said detectors. Advantageously, throughput for an inspection system in accordance with an embodiment of the invention may be increased by approximately a factor of N, where N is the number of columns in the system.

18 Claims, 11 Drawing Sheets

MULTI-PIXEL AND MULTI-COLUMN ELECTRON EMISSION INSPECTOR

CROSS-REFERENCE TO RELATED APPLICATIONS

The present application claims the benefit of provisional patent application No. 60/453,178, filed Mar. 10, 2003, entitled "Multi-Pixel and Multi-Column Electron Emission Inspector", by inventor David L. Adler, the disclosure of which is herby incorporated by reference.

BACKGROUND OF THE INVENTION

1. Field of the Invention

The present invention relates generally to microscopic inspection methods and apparatus. The present invention relates more particularly to automated inspection systems for semiconductor manufacturing.

2. Description of the Background Art

A variety of methods have been used to examine microscopic surface structures of semiconductors. These have important applications in the field of semiconductor integrated circuit (IC) fabrication, where microscopic defects at a surface layer make the difference between a good or bad IC. For example, holes or vias in an intermediate insulating layer often provide a physical conduit for an electrical connection between two outer conducting layers. If one of these holes or vias becomes clogged, it will be impossible to establish this electrical connection. Automated inspection of the semiconductors is used to ensure a level of quality control in the manufacture of the integrated circuits.

An example of an electron beam (e-beam) apparatus for an inspection system is described in U.S. Pat. No. 5,578,821, issued to Meisberger et al (the Meisberger patent). The disclosure of the Meisberger patent is hereby incorporated by reference in its entirety. FIG. 1 (corresponding to FIG. 5 in the Meisberger patent) is a simplified schematic representation of the paths of the primary, secondary, back-scatter and transmitted electrons through the electron column and collection system for electron beam inspection. In brief, FIG. 1 shows a schematic diagram of the various electron beam paths within the column and below substrate 57. Electrons are emitted radially from field emission cathode 81 and appear to originate from a very small bright point source. Under the combined action of the accelerating field and condenser lens magnetic field, the beam is collimated into a parallel beam. Gun anode aperture 87 masks off electrons emitted at unusable angles, while the remaining beam continues on to beam limiting aperture 99. An upper deflector (not depicted) is used for stigmation and alignment, ensuring that the final beam is round and that it passes through the center of the objective lens 104 comprising elements 105, 106 and 107. A condenser lens (not depicted) is mechanically centered to the axis defined by cathode 81 and beam limiting aperture 99. The deflection follows the path shown, so that the scanned, focused probe (beam at point of impact with the substrate) emerges from the objective lens 104. In High Voltage mode operation, Wien filter deflectors 112 and 113 deflect the secondary electron beam into the secondary electron detector 117. When partially transparent masks are imaged, the transmitted beam 108 passes through electrode system 123 and 124 that spreads the beam 108 before it hits the detector 129. In Low Voltage mode operation, the secondary electron beam is directed by stronger Wien filter deflections toward the low-voltage secondary electron detector 160 that may be the same detector used for backscatter imaging at high voltage. Further detail on the system and its operation is described in the Meisberger patent.

FIG. 2 is a schematic depiction of a multitude of integrated circuit (IC) dies for manufacture on a single semiconductor wafer. The semiconductor wafer 202 typically comprises a silicon wafer. The wafer 202 may be, for example, 200 mm or 300 mm in diameter. On the surface of the wafer 202, numerous integrated circuit dies 204 are manufactured thereon. The integrated circuits may comprise, for example, microprocessors, memories, digital logic, analog circuits, and other circuitry.

FIG. 3 is a schematic depiction illustrating conventional raster scanning of a conventional e-beam across a semiconductor die. The typical e-beam apparatus, such as the one depicted in FIG. 1, raster scans the e-beam across an area of a specimen to generate an image thereof (much like a conventional television raster scans a beam across the screen to generate an image frame). An example path 302 of such raster scanning across an integrated circuit die 204 is illustrated in FIG. 3.

FIG. 4 is a schematic depiction illustrating a conventional translation path 402 of a semiconductor wafer 202 under an e-beam column. The translation of the wafer under the raster-scanned e-beam may be performed, for example, in steps such that one portion of a wafer is scanned, then an adjacent portion, and so on, until all the integrated circuits 204 on the wafer have been scanned. Alternatively, if only a fraction of the integrated circuits 204 are to be inspected, the path 402 need cover only those ICs to be inspected. In either case, the translation path fully spans the area to be inspected.

SUMMARY

One embodiment of the invention pertains to a method for inspecting portion of a substrate to be inspected. The method includes directing N multi-pixel incident beams respectively onto N multi-pixel areas on the substrate. Electrons emitted from the N areas are detected in a parallel manner. Advantageously, the method includes translation of the substrate in a path that only needs to cover approximately 1/N of the portion of the substrate to be inspected.

Another embodiment of the invention relates to an inspection system for inspecting a specimen. The system includes a plurality of columns for directing a plurality of multi-pixel incident beams onto a plurality of multiple-pixel regions of the specimen. Impingement of said incident beams causes emission of electrons from the regions. The system further includes a plurality of multiple-pixel electron detectors, each said detector configured to detect in parallel electrons emitted from a plurality of pixels in one of the regions, and a plurality of processing sub-systems. Each said sub-system is configured to process data from one of said detectors.

Another embodiment of the invention relates to method for inspecting substrates with increased throughput to detect defects in at least one patterned layer thereon. The method includes directing a plurality of multi-pixel incident beams onto a plurality of multiple-pixel areas on a substrate. Each said beam impinges on a different said area. The method further includes parallel detection of electrons emitted from the plurality of areas, and parallel processing of data collected from the plurality of areas.

Another embodiment of the invention pertains to an apparatus having increased throughput for inspecting semiconductor wafers. The apparatus includes a first column for directing a first multi-pixel incident beam onto a first multiple-pixel region of a wafer, and a second column for directing a second multi-pixel incident beam onto a second multiple-pixel region of the wafer. Impingement of said first incident beam causes emission of electrons from the first region, and impingement of said second incident beam causes emission of electrons from the second region. The apparatus further includes a first multiple-pixel electron detector configured to detect in parallel electrons emitted from a plurality of pixels in the first region, and a second multiple-pixel electron detector configured to detect in parallel electrons emitted from a plurality of pixels in the second region.

DETAILED DESCRIPTION

Figure 1:
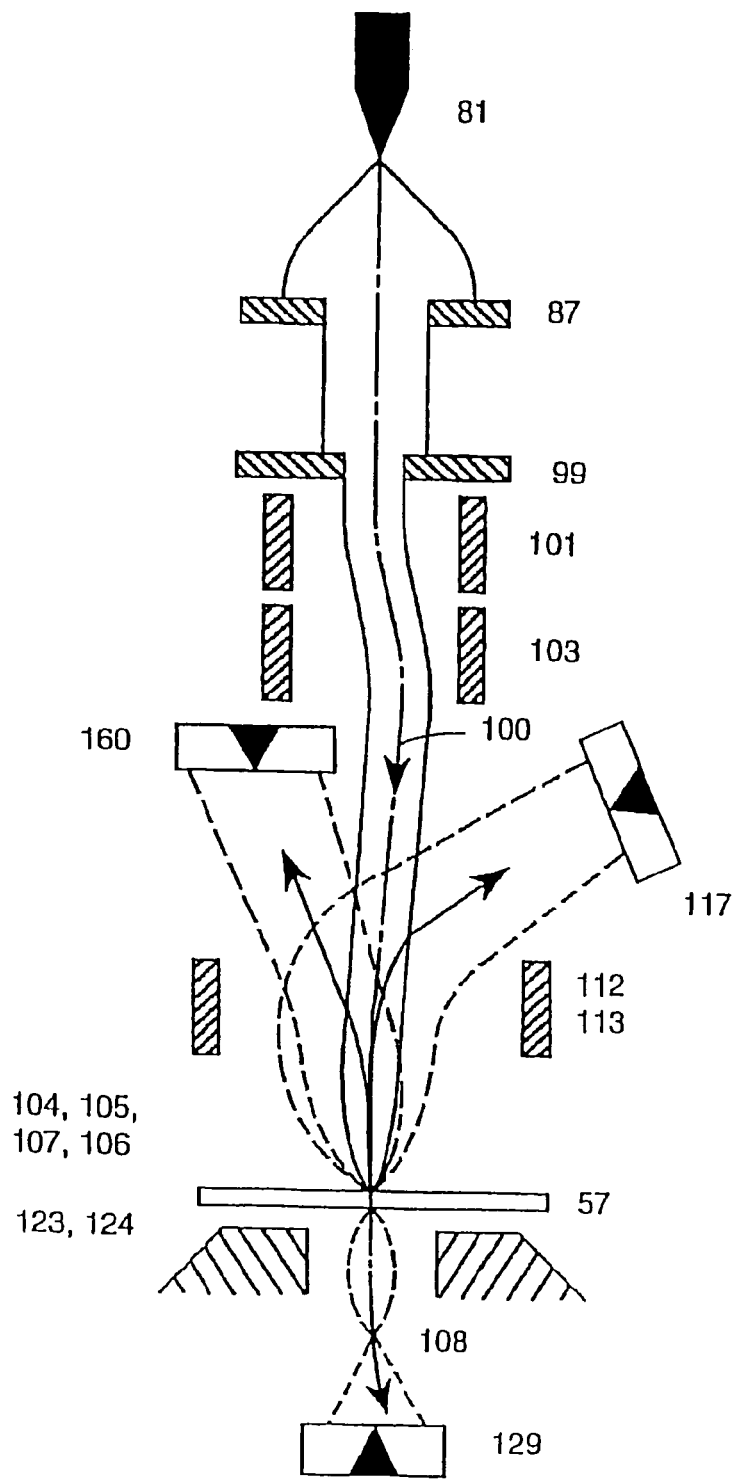
FIG. 1 illustrates an example of a conventional singular electron beam (e-beam) column for an inspection or review system.
Figure 2:
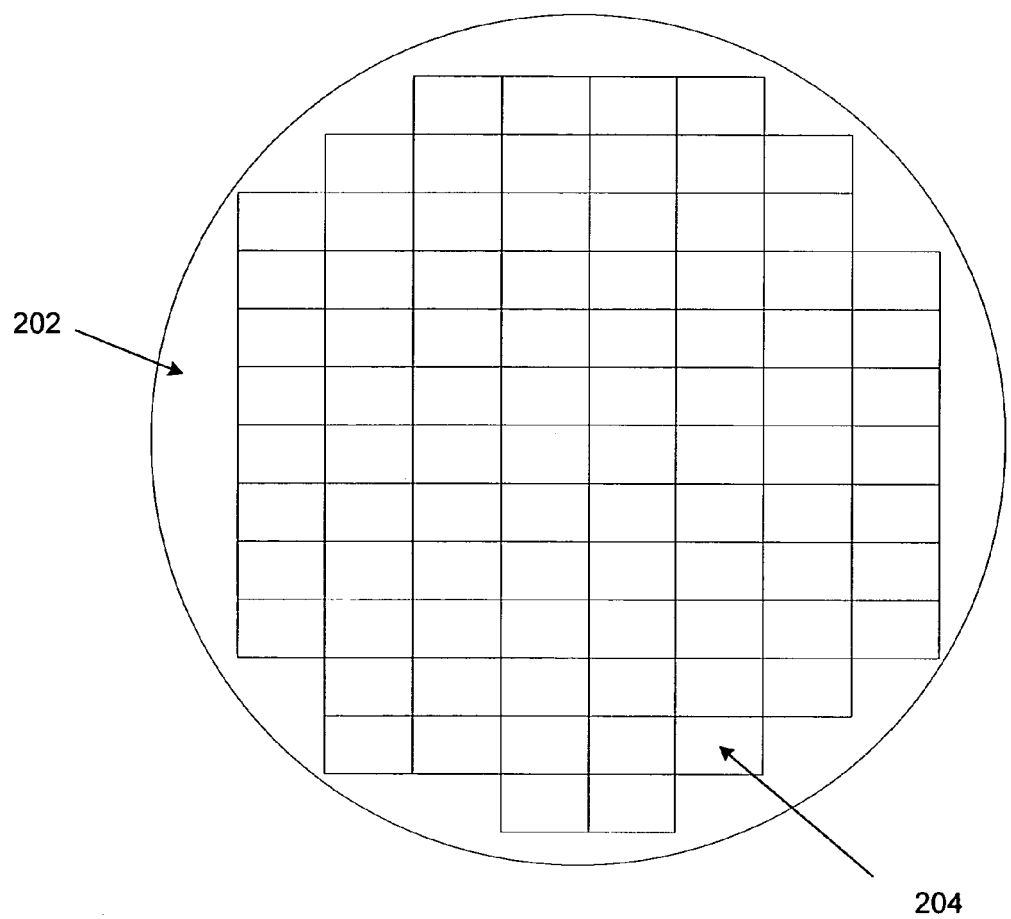
FIG. 2 is a schematic depiction of a multitude of integrated circuit dies for manufacture on a single semiconductor wafer.
Figure 3:
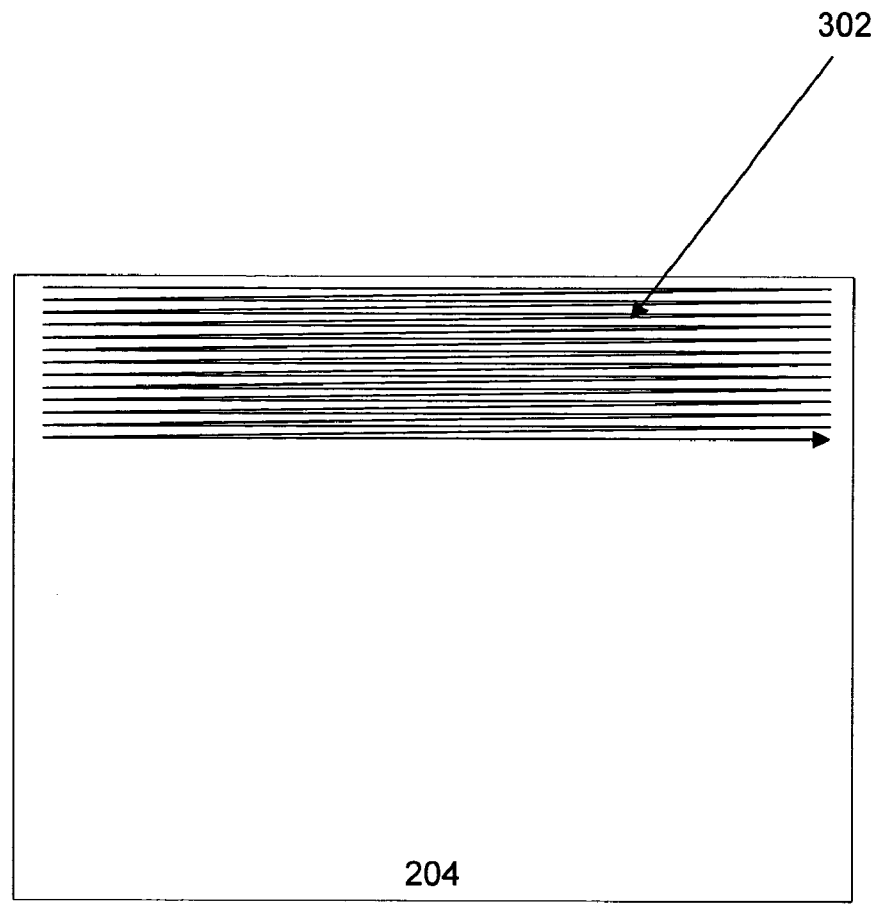
FIG. 3 is a schematic depiction illustrating conventional raster scanning of a conventional e-beam across a semiconductor die.
Figure 4:
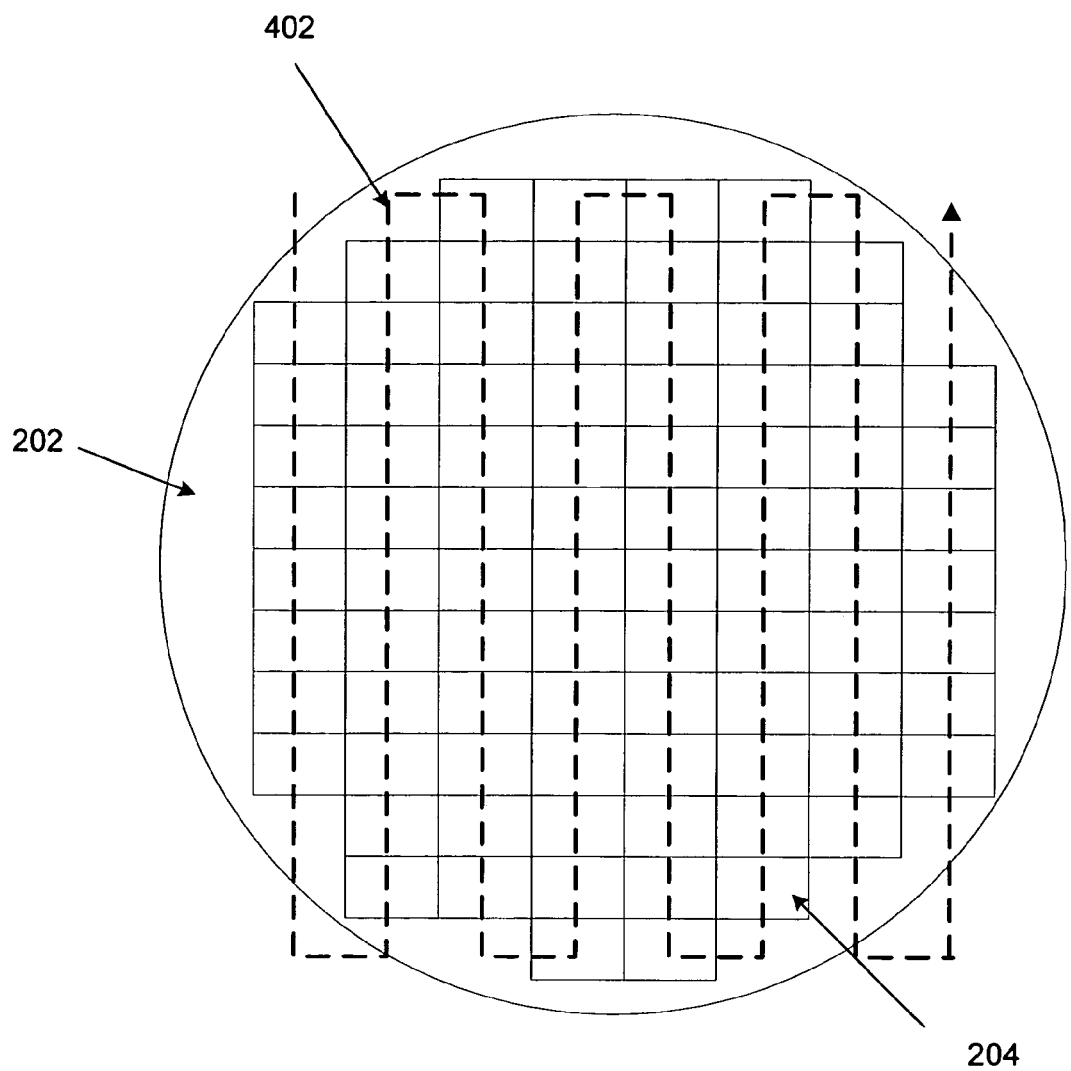
FIG. 4 is a schematic depiction illustrating a conventional translation path of a semiconductor wafer under an e-beam column.
Figure 5A:
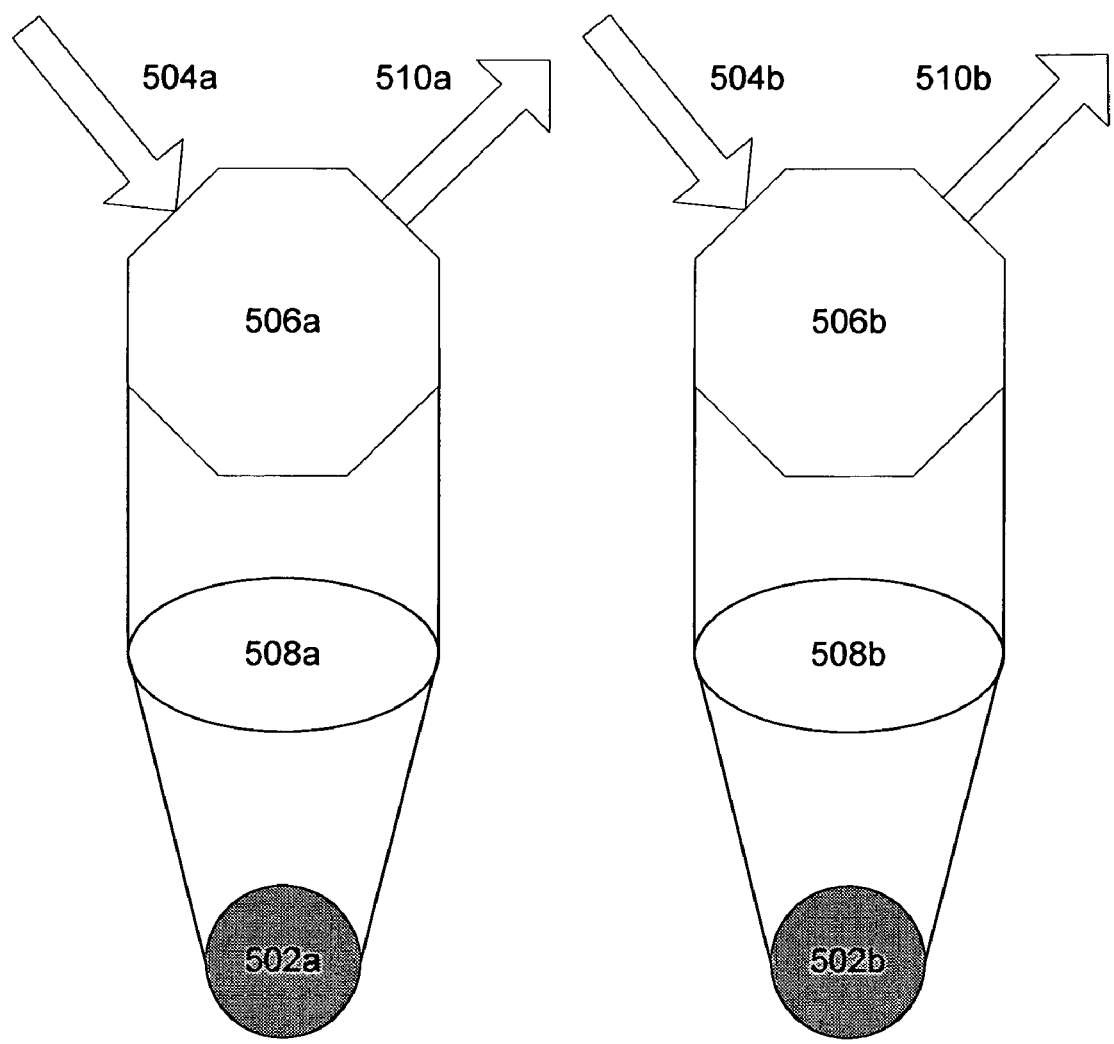
FIG. 5A schematically illustrates elements of a dual column multi-pixel e-beam apparatus in accordance with an embodiment of the invention.

FIG. 5A schematically illustrates elements of a dual column multi-pixel e-beam apparatus 500 in accordance with an embodiment of the invention. The apparatus 500 includes two columns (a and b) and forms two multi-pixel e-beam spots (502a and 502b) onto a specimen being examined. In the embodiment illustrated, each column includes at least a source, a beam separator, and an objective lens.

The two sources, one for each column, generate two incident multi-pixel beams (504a and 504b). In one embodiment, each of the sources may comprise an electron source. The electron source may be implemented, for example, using a field emission electron gun and a condenser lens system.

The two multi-pixel incident beams (504a and 504b) travel through two beam separator devices (506a and 506b, respectively). These two beam separators (506a and 506b) separate the two incident beams (504a and 504b, respectively) from the two scattered beams (510a and 510b, respectively). Each beam separator may comprise, for instance, a magnetic beam separator that bends the incident beam to be directed along the optical axis to the normal of the surface to be inspected. Alternatively, other types of beam separators may be used, for example, those in a prism type configuration.

The two incident beams (504a and 504b) subsequently travel from the two separator devices (506a and 506b, respectively) to two objective lenses (508a and 508b, respectively). Each objective lens may comprise, for example, a configuration of electromagnetic pole pieces. Alternatively, one or more of the objective lenses may be electrostatic (rather than magnetic). The two objective lenses (508a and 508b) focus the incident beams (504a and 504b, respectively) onto the two multiple-pixel areas (502a and 502b, respectively) of the specimen.

In contrast to a typical scanning electron microscope type apparatus where one single-pixel beam is scanned across an area, the apparatus 500 impinges two multiple-pixel incident beams (504a and 504b) onto the specimen. This is advantageous in that data may be obtained in parallel from the multiple pixels within each beam spot. Moreover, the use of two such multi-pixel beams (instead of just one multi-pixel beam) further increases the efficiency such that the throughput of an inspector may be further improved by approximately a factor of two.

Due to impingement of the two incident beams (504a and 504b) onto the multiple-pixel areas (502a and 502b), electrons are emitted from the surface of the areas. In a low energy electron microscopy (LEEM) embodiment, the incident electrons are decelerated between the two objective lenses (508a and 508b) and the specimen to a relatively low energy of one hundred electron volts (eV) or less, prior to impingement onto the specimen. The low-energy electrons interact with and reflect from the surface of the specimen. The reflected electrons are considered to be the scattered electrons. The scattered electrons from the two areas (502a and 502b) are then re-accelerated as they return to the two objective lenses (508a and 508b, respectively).

Subsequently, the two scattered electron beams (510a and 510b) travel from the two objective lenses (508a and 508b, respectively) to the two beam separators (506a and 506b, respectively). The two beam separators (506a and 506b) redirect the two scattered electron beams (510a and 510b, respectively) to two corresponding multi-pixel detection systems. Each multi-pixel detection system may be implemented, for example, with a charged-coupled device (CCD) array or other type of detector array.

Figure 5B:
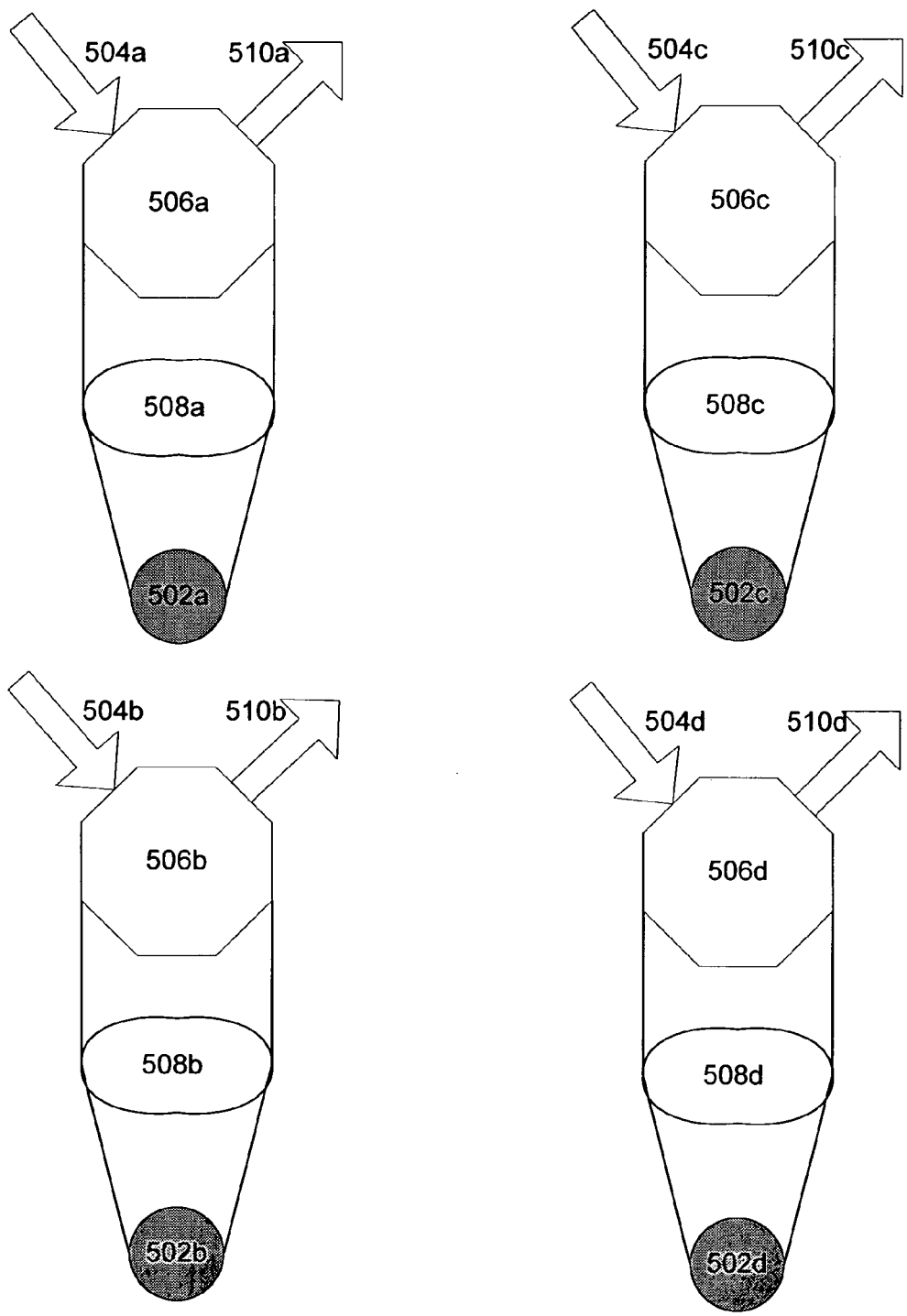
FIG. 5B schematically illustrates elements of a quad column multi-pixel e-beam apparatus in accordance with an embodiment of the invention.

FIG. 5B schematically illustrates elements of a quad column multi-pixel e-beam apparatus 550 in accordance with an embodiment of the invention. The apparatus 550 includes four columns (a, b, c, and d) and forms four multi-pixel e-beam spots (502a, 502b, 502c and 502d) onto a specimen being examined. In the embodiment illustrated, each column includes at least a source, a beam separator, and an objective lens.

The four sources, one for each column, generate four incident multi-pixel beams (504a, 504b, 504c and 504d). In one embodiment, each of the sources may comprise an electron source. The electron source may be implemented, for example, using a field emission electron gun and a condenser lens system.

The four multi-pixel incident beams (504a, 504b, 504c and 504d) travel through four beam separator devices (506a, 506b, 506c and 506d, respectively). The four beam separators (506a, 506b, 506c and 506d) separate the four incident beams (504a, 504b, 504c and 504d, respectively) from the four scattered beams (510a, 510b, 510c and 510d, respectively). Each beam separator may comprise, for instance, a magnetic beam separator that bends the incident beam to be directed along the optical axis to the normal of the surface to be inspected. Alternatively, other types of beam separators may be used, for example, those in a prism type configuration.

The four incident beams (504a, 504b, 504c and 504d) continue to travel from the four separator devices (506a, 506b, 506c and 506d, respectively) to four objective lenses (508a, 508b, 508c and 508d, respectively). Each objective lens may comprise, for example, a configuration of electromagnetic pole pieces. Alternatively, one or more of the objective lenses may be electrostatic (rather than magnetic). The four objective lenses (508a, 508b, 508c and 508d) focus the incident beams (504a, 504b, 504c and 504d, respectively) onto the multiple-pixel areas (502a, 502b, 502c and 502d, respectively) of the specimen.

In contrast to a typical scanning electron microscope type apparatus where a single-pixel beam is scanned across an area, the apparatus 550 impinges four multiple-pixel incident beams (504a, 504b, 504c and 504d) onto the specimen. This is advantageous in that data may be obtained from multiple pixels in parallel within each beam spot. Moreover, the use of four such multi-pixel beams (instead of just one multi-pixel beam) further increases the efficiency such that the throughput of an inspector may be further improved by approximately a factor of four.

Due to impingement of the four incident beams (504a, 504b, 504c and 504d) onto the four multiple-pixel areas (502a, 502b, 502c and 502d), electrons are emitted from the surface of the four areas. In a low energy electron microscopy (LEEM) embodiment, the incident electrons are decelerated between the objective lenses (508a, 508b, 508c and 508d) and the specimen to a relatively low energy of about one hundred electron volts (eV) or less, prior to impingement onto the specimen. The low-energy electrons interact with and reflect from the surface of the specimen. The reflected electrons are considered to be the scattered electrons. The scattered electrons from the four areas (502a, 502b, 502c and 502d) are then re-accelerated as they return to the four objective lenses (508a, 508b, 508c and 508d).

Subsequently, the four scattered electron beams (510a, 510b, 510c and 510d) travel from the four objective lenses (508a, 508b, 508c and 508d) to the four beam separators (506a, 506b, 506c and 506d). The four beam separators (506a, 506b, 506c and 506d) redirect the four scattered electron beams (510a, 510b, 510c and 510d) to four corresponding multi-pixel detection systems. Each multi-pixel detection system may be implemented, for example, with a charged-coupled device (CCD) array or other type of detector array.

While the above two embodiments described in detail include two and four columns, respectively, embodiments of the invention generally include systems with N columns, where N is an integer of at least two.

In a preferred embodiment, the N columns of the system are configured so as to avoid interference between the various beams. For example, the columns are separated spatially, and the components of the columns placed to avoid such interference.

In alternate embodiments of the invention, one or more photon sources may be used instead of the electron sources discussed above. The photon sources may be implemented, for example, using high-pressure mercury lamps, other types of lamp, or synchrotron radiation. Such photon sources may be configured generate incident multi-pixel photon beams that may be imaged upon multi-pixel areas of the specimen. Of course, the imaging optics for such incident photon beams would be implemented using different elements than those described above in relation to incident electron beams. In such an embodiment, electrons are emitted from the surface of the specimen due to the photoelectric effect.

Figure 6:
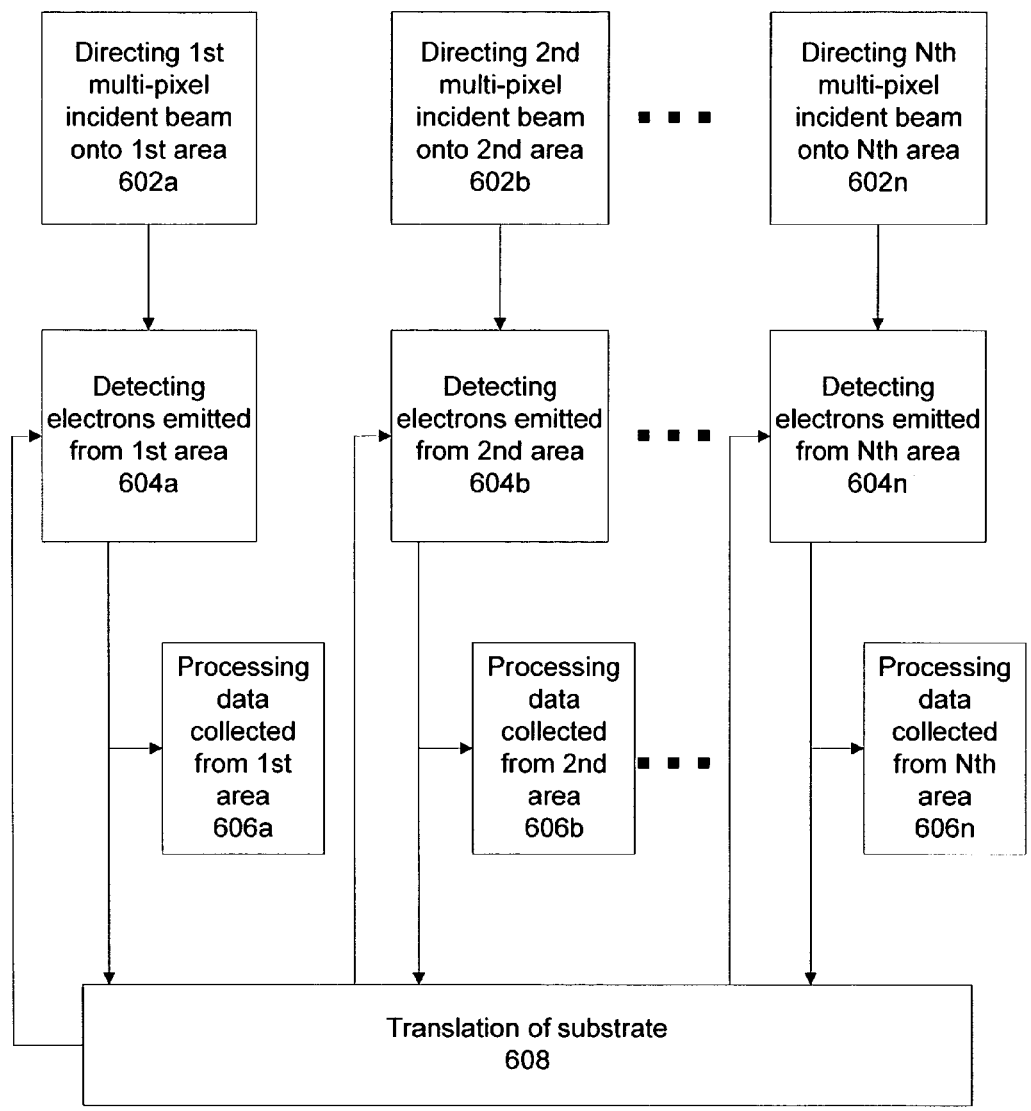
FIG. 6 is a flow chart that depicts a method for e-beam inspection with increased throughput in accordance with an embodiment of the invention.

FIG. 6 is a flow chart that depicts a process 600 for e-beam inspection with increased throughput in accordance with an embodiment of the invention. The process 600 includes N sub-processes (a, b, . . . , n) where N is at least two.

The N sub-processes (a, b, . . . , n) each begin with a first step (602a, 602b, . . . , 602n, respectively). In these first steps, N multi-pixel incident beams (e.g., 504a, 504b, . . . , 504n) are directed onto N areas (e.g., 502a, 502b, . . . , 502n) of the specimen being inspected.

Next, a second step (604a, 604b, . . . , 604n) is performed in each of the N sub-processes (a, b, . . . , n). In these second steps, electrons emitted from the N impinged areas (e.g., 502a, 502b, . . . , 502n) are detected (604a, 604b, . . . , 604n, respectively). In a preferred embodiment, such detection is advantageously performed in a parallel manner for both the N beam spots and the multiple pixels within each beam spot.

Subsequently, a third step (606a, 606b, . . . , 606n) is performed in each of the N sub-processes (a, b, . . . , n). In these third steps, data collected from the N areas (e.g., 502a, 502b, . . . , 502n) are processed. In a preferred embodiment, the processing is advantageously performed in a parallel manner using a separate processor for each of the N beam spots. For example, data from the N columns may be processed in an adaptation of computer systems that are commercially available from Mercury Computer Systems or SKY Computers, both having a place of business in Chelmsford, Mass. Such computer systems include multiple processors that may be configured to work in parallel on different image segments. For example, data from different columns may be sent independently to different sets of processors and handled in a parallel manner. In accordance with an embodiment of the invention, The processing may involve comparison of the collected data from each area with another set of data. For example, data collected from an area may be compared against reference data obtained from a known good die. The comparison between the data may involve, for example, alignment of the two data sets, differencing of the two data sets, filtering of the resultant difference data, and determination and location of apparent defects from the filtered difference data.

The above-described parallel detection and parallel processing of the data across the N beam spots is particularly advantageous in that the efficiency of the inspection technique may be increased by approximately a factor of N.

In the embodiment illustrated in FIG. 6, the process 600 also includes translation 608 of the specimen so as to effectively move the N areas being impinged by the N incident beams in different swaths across the specimen being examined. Example paths for such translation 608 are described below.

Figure 7A:
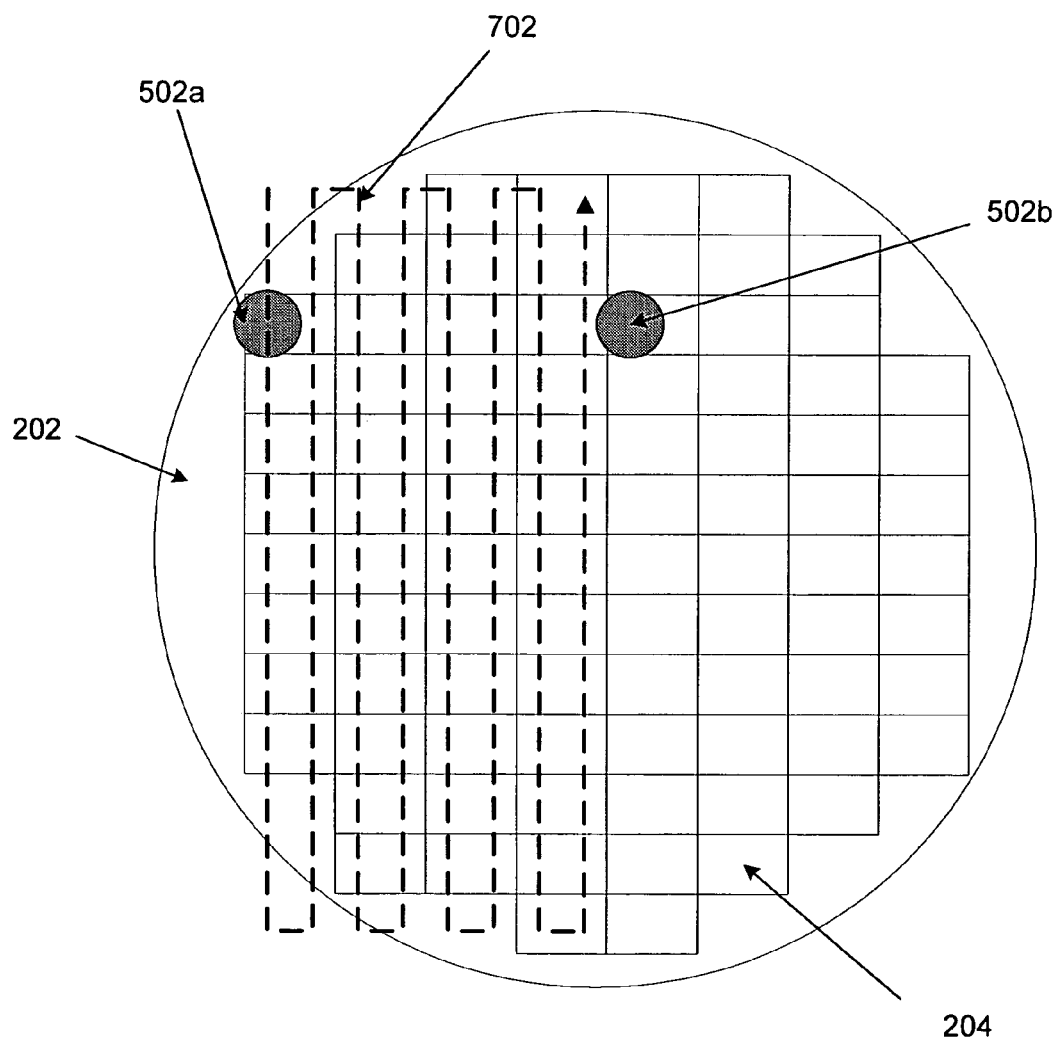
FIG. 7A depicts a translation path that covers approximately one half of a specimen during an inspection of the entire specimen in accordance with an embodiment of the invention.

FIG. 7A depicts a translation path 702 that covers approximately one half of a specimen during an inspection of the entire specimen in accordance with an embodiment of the invention. Depicted as an example specimen is a semiconductor wafer 202 with numerous integrated circuit dies 204 being manufactured thereon. In this case, two multi-pixel beam spots (502a and 502b) are being impinged by two columns onto separate areas of the wafer 202. Translation 608 of the wafer 202 may occur, for example, on the path 702 depicted in FIG. 7A. In one embodiment, the translation 608 along the path 702 may be performed in a step-wise manner to move the two beam spots (502a and 502b) across the desired areas of the substrate 202. Alternatively, the translation 608 may be continuous, in which case the data detection (604a and 604b) and/or the data processing (606a and 606b) would have to be configured to take into account the continuous movement. Advantageously, the example translation path 702 covers only about half the wafer 202, while the data is being collected from the entire wafer 202. This provides for an increased throughput by approximately a factor of two in comparison with a single column system.

Figure 7B:
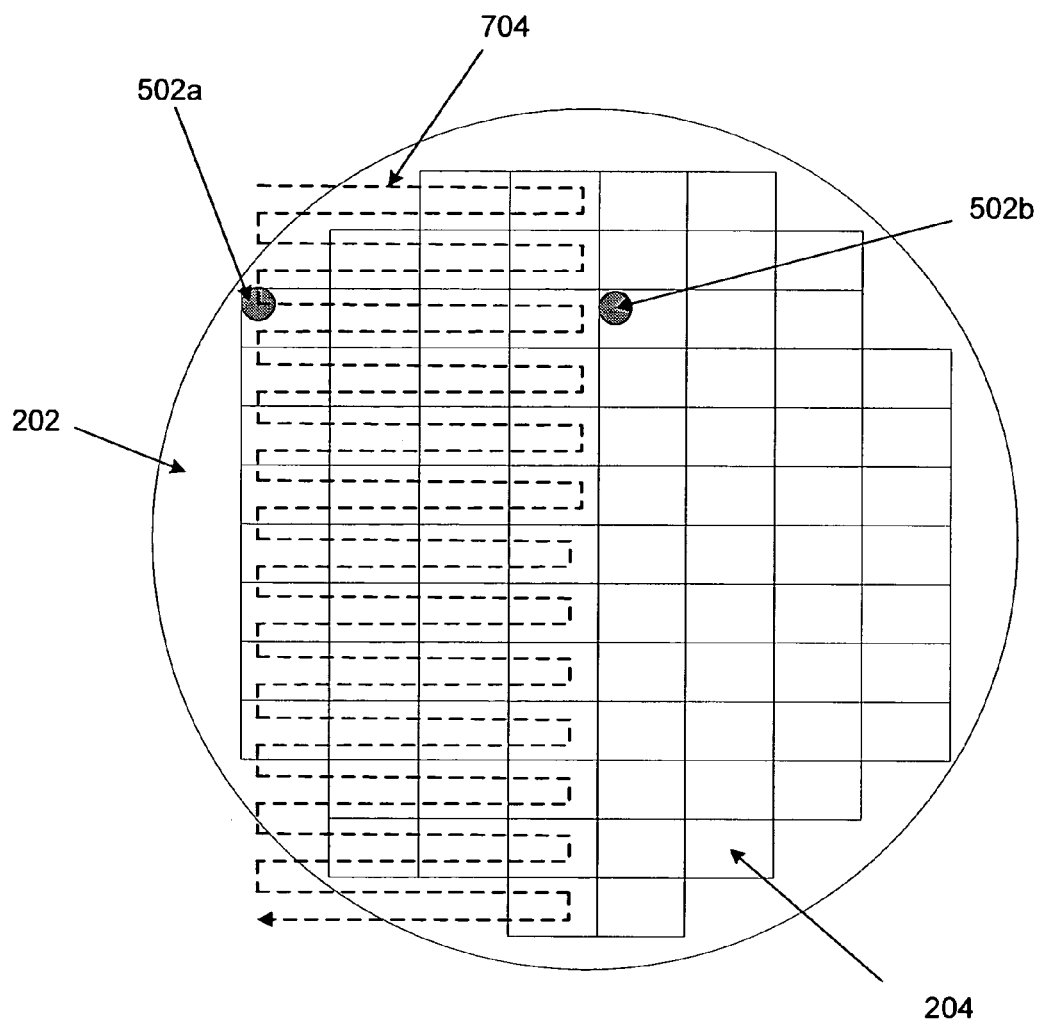
FIG. 7B depicts another translation path that covers approximately one half of a specimen during an inspection of the entire specimen in accordance with an embodiment of the invention.

FIG. 7B depicts another translation path 704 that covers approximately one half of a specimen during an inspection of the entire specimen in accordance with an embodiment of the invention. Similarly, this translation path 704 covers only about half the wafer 202, while the data is being collected from the entire wafer 202. Again, this provides for an increased throughput by approximately a factor of two in comparison with a single column system.

Figure 8A:
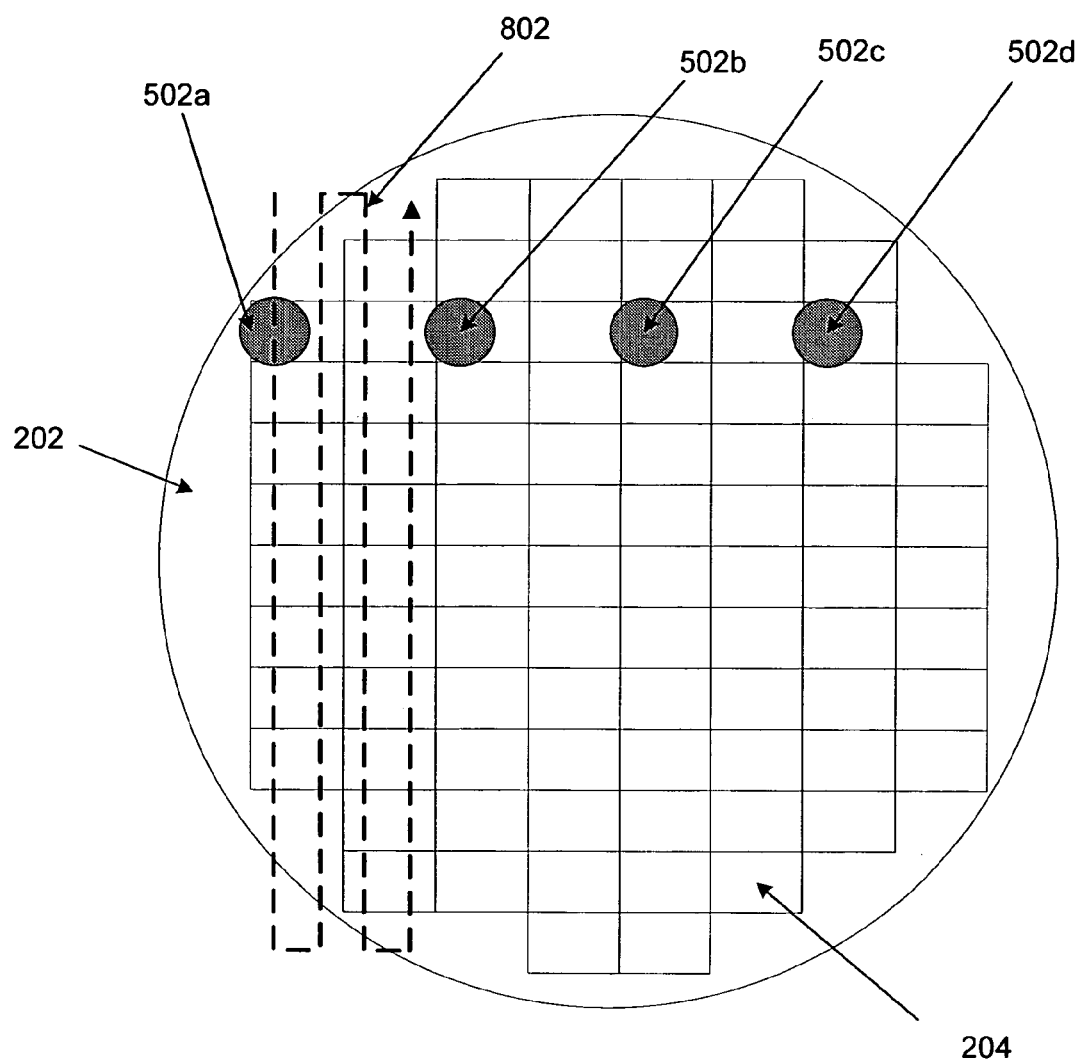
FIG. 8A depicts a translation path that covers approximately one fourth of a specimen during an inspection of the entire specimen in accordance with an embodiment of the invention.

FIG. 8A depicts a translation path 802 that covers approximately one fourth of a specimen during an inspection of the entire specimen in accordance with an embodiment of the invention. In this case, four multi-pixel beam spots (502a, 502b, 502c and 502d) are being impinged by four columns onto separate areas of the wafer 202. Translation 608 of the wafer 202 may occur, for example, on the path 802 depicted in FIG. 8A. In one embodiment, the translation 608 along the path 802 may be performed in a step-wise manner to move the four beam spots (502a, 502b, 502c and 502d) across the desired areas of the substrate 202. Alternatively, the translation 608 may be continuous, in which case the data detection (604a, 604b, 604c and 604d) and/or the data processing (606a, 606b, 606c and 606d) would have to be configured to take into account the continuous movement. Advantageously, the example translation path 802 covers only about a quarter of the wafer 202, while the data is being collected from the entire wafer 202. This provides for an increased throughput by approximately a factor of four in comparison with a single column system.

Figure 8B:
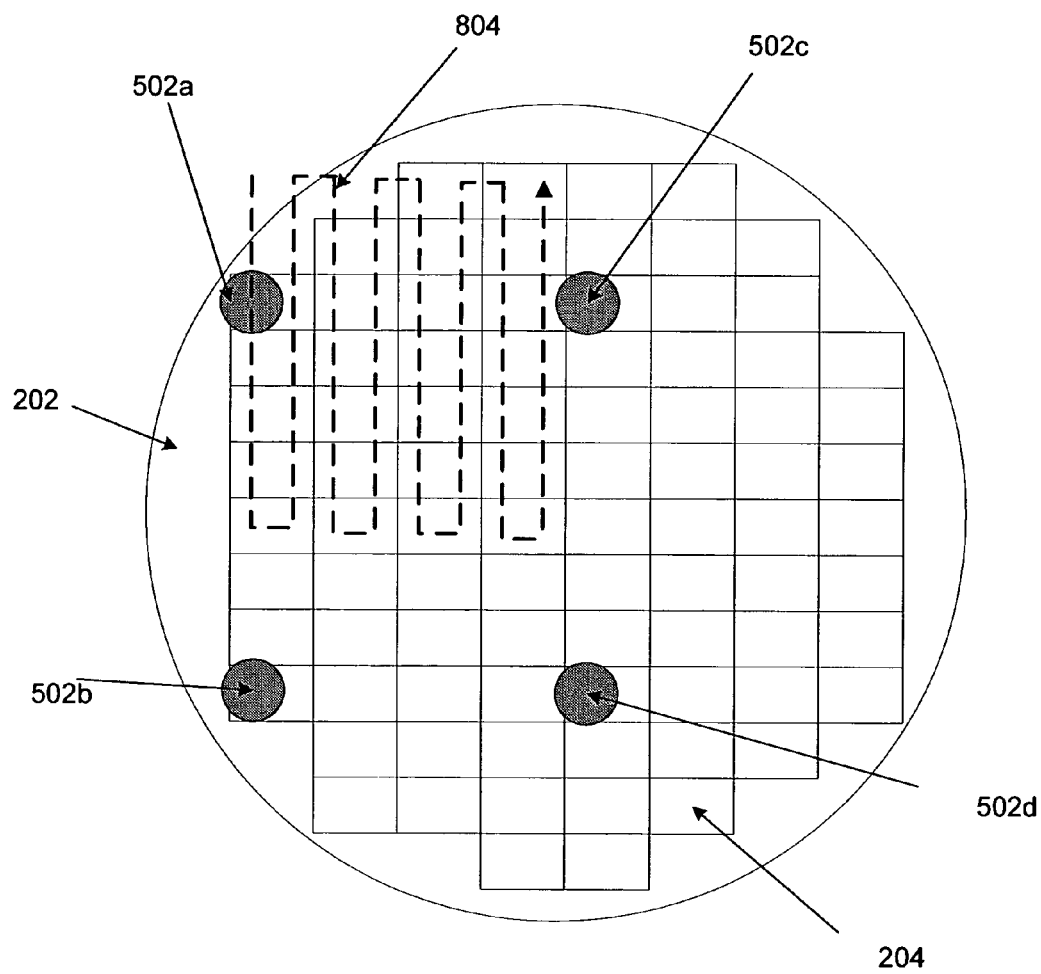
FIG. 8B depicts another translation path that covers approximately one fourth of a specimen during an inspection of the entire specimen in accordance with an embodiment of the invention.

FIG. 8B depicts another translation path 804 that covers approximately one fourth of a specimen during an inspection of the entire specimen in accordance with an embodiment of the invention. Similarly, this translation path 804 covers only about a quarter of the wafer 202, while the data is being collected from the entire wafer 202. Again, this provides for an increased throughput by approximately a factor of four in comparison with a single column system.

Note that in the above illustrations (FIGS. 7A, 7B, 8A and 8B), the beam spots are depicted as spanning approximately half of a dimension of a circuit die. The beam spots, of course, need not be of that size. The beam spot size would depend on the particular implementation of the columns. Implemented beam spot sizes may range from a small fraction of a die or may even be greater in size than a die. The above-described translation paths would be adjusted accordingly in dependence on the particular beam spot size.

The above-described diagrams are not necessarily to scale and are intended be illustrative and not limiting to a particular implementation. The above-described invention may be used in an automatic inspection or review system and applied to the inspection or review of wafers, X-ray masks and similar substrates in a production environment. While it is expected that the predominant use of the invention will be for the inspection or review of wafers, optical masks, X-ray masks, electron-beam-proximity masks and stencil masks, the techniques disclosed here may be applicable to the high speed electron beam imaging of other samples.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for inspecting portion of a substrate to be inspected, the method comprising:
    generation of N multi-pixel incident electron beams;
    directing the N multi-pixel incident electron beams through N beam separators in a first direction;
    focusing the N multi-pixel incident electron beams onto N beam spots on the substrate, wherein multiple pixels are included within each beam spot;
    directing electrons emitted from the N beam spots through the N beam separators in a second direction so as to separate the emitted electrons from the incident beams;
    detecting the emitted electrons using N multi-pixel detector arrays, wherein each detector array detects multiple pixels from one of the beam spots in a parallel manner; and
    translation of the substrate in a path that covers approximately 1/N of the portion of the substrate to be inspected.

2. The method of claim 1, wherein the portion of the substrate to be inspected comprises all integrated circuit dies on a wafer.

3. The method of claim 1, wherein the portion of the substrate to be inspected comprises a fraction of dies on a wafer.

4. An inspection system for inspecting a specimen, the system comprising:
    a plurality of electron sources, each said source configured to generate a multi-pixel incident beam;

a plurality of objective lenses, each said objective lens configured to focus a multi-pixel incident beam onto a corresponding beam spot on the specimen, wherein multiple pixels are included within each beam spot and impingement of said incident beam causes emission of electrons from the beam spot; and a plurality of multiple-pixel electron detectors, each said detector configured to detect the multiple pixels in parallel from electrons emitted from one of the beam spots; and a plurality of beam separators, each said separator configured to direct one of the multi-pixel incident beams in a first direction from a corresponding electron source to a corresponding objective lens and to direct said emitted electrons in a second direction from the corresponding objective lens to a corresponding multiple-pixel electron detector.

5. The system of claim 4, further comprising a translation mechanism for translating the wafer under said plurality of incident beams such that the corresponding beam spots are scanned across the wafer.

6. A method for inspecting substrates with increased throughput to detect defects in at least one patterned layer thereon, the method comprising:

providing a plurality of multi-pixel incident beams;

directing the incident beams towards a surface of a substrate;

emission of electrons due to impingement of the incident beams onto beam spots on the surface;

bending said emitted electrons towards a plurality of multi-pixel detector arrays so as to separate said emitted electrons from the incident beams;

detecting in parallel said emitted electrons from said beam spots using the plurality of detector arrays, wherein each detector array detects multiple pixels from one of the beam spots in a parallel manner; and processing in parallel data collected by the plurality of detector arrays.

7. The method of claim 6, further comprising:

translation of the substrate in a path such that the plurality of incident beams are scanned across the surface of the substrate.

8. The method of claim 7, wherein the plurality of incident beams comprises N incident beams, and wherein an inspected area during the translation comprises approximately N times an area covered by a translation path of a single beam spot.

9. The method of claim 8, wherein N is at least two.

10. The method of claim 9, wherein N is no more than fifty.

11. The method of claim 6, wherein at least one incident beam comprises incident electrons.

12. The method of claim 6, wherein the processing in parallel comprises comparison of the collected data from each detector array with another set of data.

13. The method of claim 12, wherein the comparison comprises alignment, differencing, filtering, and defect location.

14. An electron-emission inspector apparatus having increased throughput for inspecting semiconductor wafers, the apparatus comprising:

a first column for directing a first multi-pixel incident beam onto a first multiple-pixel beam spot of a wafer, wherein impingement of said first incident beam causes emission of electrons from the first beam spot so as to generate a first multi-pixel emitted beam;

a first multiple-pixel electron detector configured to detect in parallel pixels of the first multi-pixel emitted beam;

a first beam separator in the first column which is configured to separate the first multi-pixel emitted beam from the first multi-pixel incident beam;

a second column for directing a second multi-pixel incident beam onto a second multiple-pixel beam spot of the wafer, wherein impingement of said second incident beam causes emission of electrons from the second beam spot so as to generate a second multi-pixel emitted beam;

a second multiple-pixel electron detector configured to detect in parallel pixels of the second multi-pixel emitted beam; and a second beam separator in the second column which is configured to separate the second multi-pixel emitted beam from the second multi-pixel incident beam.

15. The apparatus of claim 14, further comprising:

a first processor system for processing data from said first detector to inspect for defects; and a second processor system for processing data from said second detector to inspect for defects.

16. The apparatus of claim 15, further comprising a translation system for translating the wafer under said first and second incident beams such that the first and second multiple-pixel beam spots are scanned across the wafer.

17. The apparatus of claim 14, wherein the first and second incident beams each comprises incident electrons, and wherein the first and second columns each further comprise an objective lens.

18. The apparatus of claim 17, wherein the electrons emitted from the first and second beam spots comprise secondary electrons.

* * * * *